United States Patent
Hayden, Jr. et al.

(10) Patent No.: US 7,894,652 B2
(45) Date of Patent: Feb. 22, 2011

(54) PROMPT GAMMA CORRECTION FOR NON-STANDARD ISOTOPES IN A PET SCANNER

(75) Inventors: Charles H. Hayden, Jr., Knoxville, TN (US); Michael E. Casey, Louisville, TN (US); Charles C. Watson, Knoxville, TN (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 543 days.

(21) Appl. No.: 12/110,474

(22) Filed: Apr. 28, 2008

(65) Prior Publication Data

US 2008/0283758 A1 Nov. 20, 2008

Related U.S. Application Data

(60) Provisional application No. 60/914,419, filed on Apr. 27, 2007.

(51) Int. Cl.
G06K 9/00 (2006.01)
G01R 23/02 (2006.01)
G01N 23/00 (2006.01)

(52) U.S. Cl. .................. 382/128; 250/250; 250/362; 250/384; 378/1

(58) Field of Classification Search ......... 382/128–132; 250/250–266, 362, 384; 378/1–37
See application file for complete search history.

(56) References Cited

U.S. PATENT DOCUMENTS

| | | | | |
|---|---|---|---|---|
| 5,608,221 A * | 3/1997 | Bertelsen et al. | ........ | 250/363.03 |
| 5,821,541 A * | 10/1998 | Tumer | .................. | 250/370.09 |
| 5,834,779 A * | 11/1998 | Shao et al. | ............. | 250/363.03 |
| 6,072,177 A * | 6/2000 | McCroskey et al. | ...... | 250/252.1 |
| 6,410,920 B1 * | 6/2002 | Shao et al. | ............. | 250/363.04 |
| 6,420,711 B2 * | 7/2002 | Tumer | .................. | 250/370.09 |
| 6,448,560 B1 * | 9/2002 | Tumer | .................. | 250/370.09 |
| 7,022,995 B2 * | 4/2006 | Tumer | .................. | 250/370.09 |
| 7,345,284 B2 * | 3/2008 | Tumer | .................. | 250/370.09 |
| 7,777,189 B2 * | 8/2010 | Schweizer et al. | ..... | 250/363.04 |
| 2002/0036270 A1 * | 3/2002 | Tumer | .................. | 250/370.09 |
| 2005/0173643 A1 * | 8/2005 | Tumer | .................. | 250/370.09 |
| 2008/0224050 A1 * | 9/2008 | Thielemans et al. | ......... | 250/362 |
| 2009/0057561 A1 * | 3/2009 | Schweizer et al. | ..... | 250/363.04 |

* cited by examiner

*Primary Examiner*—Manav Seth
(74) *Attorney, Agent, or Firm*—Peter L. Kendall

(57) ABSTRACT

A method for correcting PET emission data for prompt gamma emission background components present in non-pure positron-emitting isotopes uses a two component fit of modeled scatter and modeled prompt gamma emission in the area of scatter tails in a normalized emission sinogram. The method allows a PET scan using non-standard PET isotopes to be quantitative and thus more clinically useful.

15 Claims, 4 Drawing Sheets

| | PROCESS | INPUT | OUTPUT |
|---|---|---|---|
| 110 | PREPARE THE INPUT DATA CONVERT FROM DICOM TO INTERFILE IF NEEDED | DICOM DATA | em.s, .hdr norm.n, .hdr attn.a, .hdr |
| 120 | NORMALIZE THE SCAN (WITHOUT SCATTER OR ATTENUATION CORRECTION) | em.s norm.n | emc.s |
| 130 | ESTIMATE THE SCATTER | emc.s attn.a | scat.s |
| 140 | FIND THE SINOGRAM TAILS | attn.a | tails.s |
| 150 | CREATE A RANDOMS SINOGRAM FROM THE SINGLES | em.hdr | randoms.s |
| 160 | LSF THE TAILS AND REMOVE BACKGROUND (BACKGROUND MODELED AS LINEAR COMBINATION OF RANDOMS AND SCATTER) CLEAN = Emc(t) - k*Randoms(t) - j*Scatter(t) | emc.s randoms.s scat.s tails.s | clean.s |
| 170 | ATTENUATION CORRECT (WITHOUT SCATTER OR NORMALIZATION) | clean.s attn.a | final.s |
| 180 | RECONSTRUCT THE FULLY CORRECTED SINOGRAM | final.s | image.v |

| | PROCESS | INPUT | OUTPUT |
|---|---|---|---|
| 110 | PREPARE THE INPUT DATA<br>CONVERT FROM DICOM TO INTERFILE IF NEEDED | DICOM DATA | em.s, .hdr<br>norm.n, .hdr<br>attn.a, .hdr |
| 120 | NORMALIZE THE SCAN<br>(WITHOUT SCATTER OR ATTENUATION CORRECTION) | em.s<br>norm.n | emc.s |
| 130 | ESTIMATE THE SCATTER | emc.s<br>attn.a | scat.s |
| 140 | FIND THE SINOGRAM TAILS | attn.a | tails.s |
| 150 | CREATE A RANDOMS SINOGRAM FROM THE SINGLES | em.hdr | randoms.s |
| 160 | LSF THE TAILS AND REMOVE BACKGROUND<br>(BACKGROUND MODELED AS LINEAR COMBINATION<br>OF RANDOMS AND SCATTER)<br>CLEAN = Emc(t) - k*Randoms(t) - j*Scatter(t) | emc.s<br>randoms.s<br>scat.s<br>tails.s | clean.s |
| 170 | ATTENUATION CORRECT<br>(WITHOUT SCATTER OR NORMALIZATION) | clean.s<br>attn.a | final.s |
| 180 | RECONSTRUCT THE FULLY CORRECTED SINOGRAM | final.s | image.v |

FIG. 1

PROMPT GAMMA CORRECTION FOR NON-STANDARD ISOTOPES IN A PET SCANNER

CROSS-REFERENCE TO RELATED APPLICATION AND CLAIM OF PRIORITY

This application is a non-provisional under 35 U.S.C. §119 (e) and claims priority of Provisional Application Ser. No. 60/914,419 filed Apr. 27, 2007.

TECHNICAL FIELD

The current invention is in the field of nuclear medical imaging. Particularly, the invention relates to techniques for correction of image acquisition data in Positron Emission Tomography (PET) to enable PET scans to be quantitative.

BACKGROUND OF THE INVENTION

Medical imaging is one of the most useful diagnostic tools available in modern medicine. Medical imaging allows medical personnel to non-intrusively look into a living body in order to detect and assess many types of injuries, diseases, conditions, etc. Medical imaging allows doctors and technicians to more easily and correctly make a diagnosis, decide on a treatment, prescribe medication, perform surgery or other treatments, etc.

There are medical imaging processes of many types and for many different purposes, situations, or uses. They commonly share the ability to create an image of a bodily region of a patient, and can do so non-invasively. Examples of some common medical imaging types are nuclear medical (NM) imaging such as positron emission tomography (PET) and single photon emission computed tomography (SPECT). Using these or other imaging types and associated machines, an image or series of images may be captured. Other devices may then be used to process the image in some fashion. Finally, a doctor or technician may read the image in order to provide a diagnosis.

A PET camera works by detecting pairs of gamma ray photons in time coincidence. The two photons arise from the annihilation of a positron and electron in the patient's body. The positrons are emitted from a radioactive isotope that has been used to label a biologically important molecule like glucose (a radiopharmaceutical). Hundreds of millions such decays occur per second in a typical clinical scan. Because the two photons arising from each annihilation travel in opposite directions, the rate of detection of such coincident pairs is proportional to the amount of emission activity, and hence glucose, along the line connecting the two detectors. In a PET camera the detectors are typically arranged in rings around the patient. By considering coincidences between all appropriate pairs of these detectors, a set of projection views can be formed each element of which represents a line integral, or sum, of the emission activity in the patient's body along a well defined path. These projections are typically organized into a data structure called a sinogram, which contains a set of plane parallel projections at uniform angular intervals around the patient. A three dimensional image of the radiopharmaceutical's distribution in the body can then be reconstructed from these data.

Most PET scans are performed using pure positron emitters, and can be made quantitative by performing normalization, attenuation correction and scatter correction processes on the acquired image data. Single gamma background can be removed from the image data acquisition of such pure positron emitter isotopes through the use of time-coincidence detection. However, there are isotopes that decay through the emission of a positron while the nucleus remains in an excited angular momentum state, leading to a prompt gamma emission (e.g., within about 0.1 nsec of the annihilation gamma pair in liquids or solids and 10-100 nsec in atmospheric air). This solitary gamma plus the two annihilation gamma photons (E=511 keV) derived from a positron-electron annihilation yields a triple of coincident gammas with known energies. Thus the net decay signature is a 511 keV gamma pair traveling in opposite directions and a solitary gamma with a non-correlated emission direction and distinct energy. When a non-standard PET isotope is used, therefore, the prompt gamma background component additionally must be compensated for in the acquired data.

Prior efforts have attempted to compensate for the prompt gamma component by using a flat background or a modeled prompt gamma distribution in the non-scatter tails of the sinogram representation of the acquired projection data. Such methods however have proven to be inaccurate.

SUMMARY OF THE INVENTION

In accordance with the present invention a method of correcting acquired PET projection data is provided that achieves an accurate quantification of a PET scan obtained using non-standard PET isotopes. In particular, a two-component fit of modeled scatter and modeled prompt gamma emission is carried out in the area of scatter tails in a normalized emission sinogram. The scatter tail area provides better statistics for the fit, thus resulting in a better match to the data and a more accurate quantification of the PET emission data.

BRIEF DESCRIPTION OF THE DRAWINGS

The invention will now be described in greater detail in the following by way of example only and with reference to the attached drawings, in which:

FIG. 1 is a table illustrating steps of a method in accordance with an embodiment of the current invention;

DETAILED DESCRIPTION OF THE INVENTION

As required, disclosures herein provide a detailed embodiment of the present invention; however, the disclosed embodiment is merely exemplary of the invention that may be embodied in various and alternative forms. Therefore, there is no intent that specific structural and functional details should be limiting, but rather the intention is that they provide a basis for the claims and as a representative basis for teaching one skilled in the art to variously employ the present invention.

FIG. 1 is a table of a method according to the present invention. At step 110, nuclear medical image projection data is obtained from a PET scanner. The data is conventionally sent to a processor from the PET scanner in the DICOM (Digital Imaging and Communications in Medicine) standard. The data may be converted from the DICOM standard to another standard, such as Interfile, if needed. The processor generates from the inputted DICOM data from the PET scanner an emission sinogram (em.s), attenuation factors (attn.a), and normalization factors (norm.n), together with associated headers (.hdr). In one embodiment, the attenuation data is obtained from a CT scanner used to obtain attenuation data, but the attenuation data also could come from the PET scan itself or any other imaging modality that may be merged with the PET scanner, e.g. MR/PET, SPECT/PET, CT/PET etc.

Figure 2A:
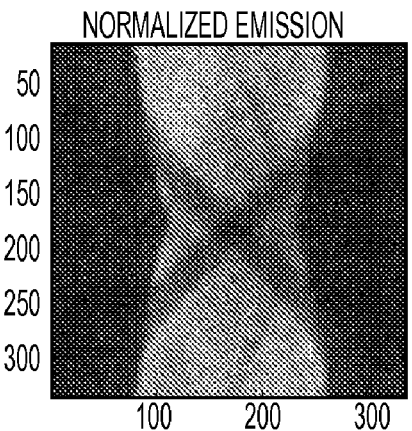
FIGS. 2A-2E depict images of various PET image data distributions at different steps of the method.
Figure 3A:
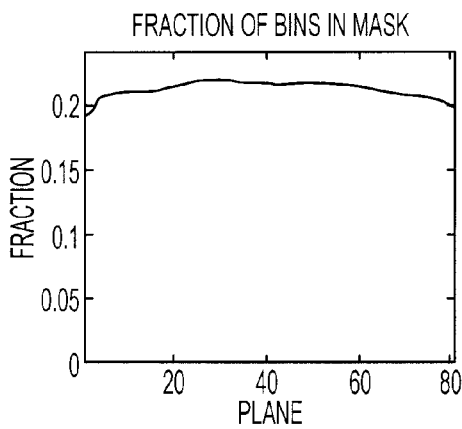
FIGS. 3A-3E are graphs of various model factor profiles used in the compensation method in accordance with an embodiment of the invention.
Figure 3B:
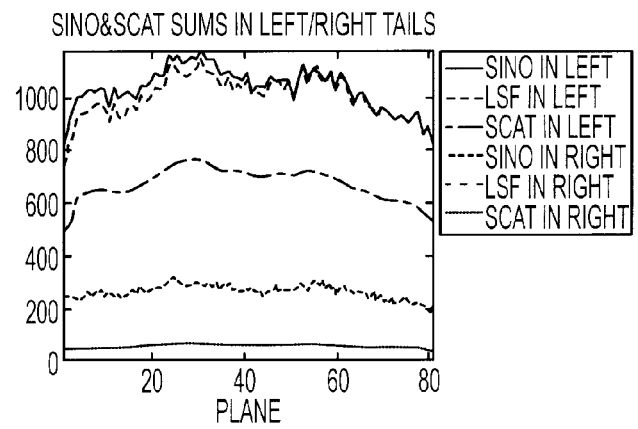
Figure 3C:
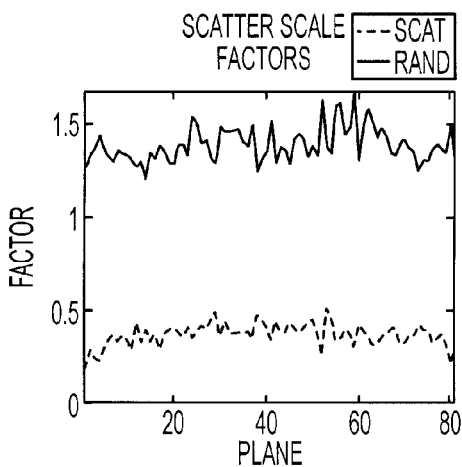
Figure 3D:
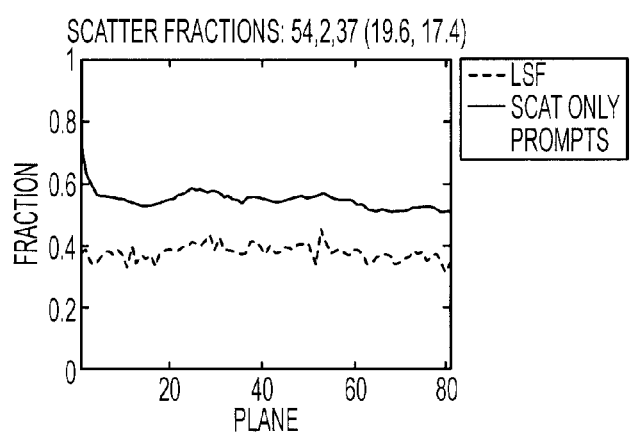

At step 120, the emission sinogram em.s (i.e., without scatter or attenuation correction) is normalized using the normalization factors norm.n, to obtain a normalized emission sinogram (emc.s). See FIGS. 2A, 3A. At step 130, the contribution of scatter to the emission data is estimated using the attenuation factors attn.a in a scatter simulation on the normalized emission sinogram emc.s, to obtain a scatter sinogram (scat.s). See FIGS. 2C, 3B, 3C, 3D.

Figure 2B:
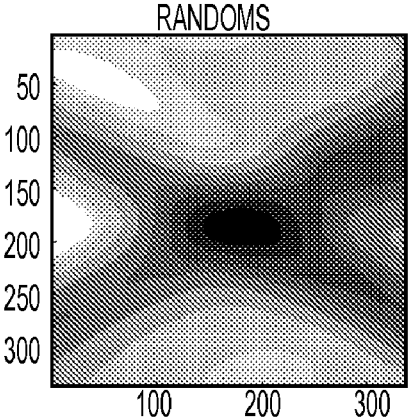
Figure 2C:
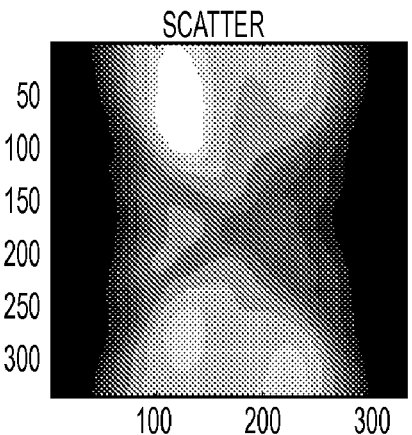
Figure 3E:
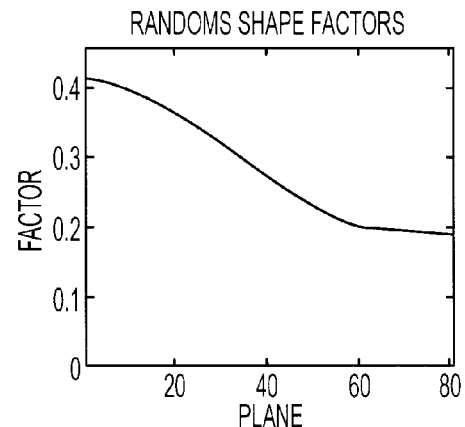

At step 140, the sinogram tails are found using the attenuation and scatter sinograms, to obtain a tails sinogram tails.s. At step 150, A randoms sinogram randoms.s is generated from the singles rates in the emission sinogram header (em.hdr). See FIGS. 2B, 3E. This randoms sinogram serves as the model of the prompt gamma component of the emission data. However, it is to be noted that the prompt gamma model may be constructed from other suitable data that accurately represents the contribution of prompt gamma emission to the collected PET data. For example, the prompt gamma background may be estimated using smoothed randoms (e.g. data from the scanner), or using a computer simulation based on scanner data and isotope.

Next, at step 160 the background radiation is removed from the normalized emission sinogram. This background is modeled as a linear combination of the randoms (random.s) and the scatter (scat.s). These two components are used in a least-squares fit with the sinogram tails (tails.s), to obtain a "clean" sinogram (clean.s) in accordance with the following equation, wherein k and j are appropriate compensation coefficients:

$$\text{clean} = emc(t) - k^* \text{randoms}(t) - j^* \text{scat}(t) \quad (1)$$

Figure 2D:
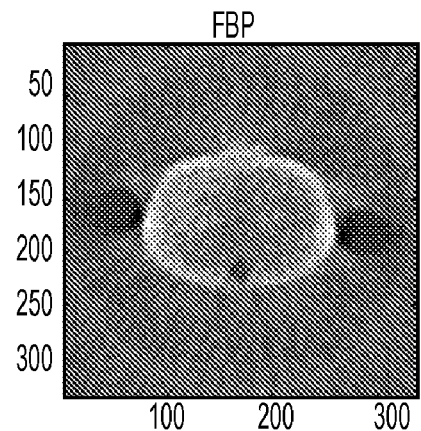
Figure 2E:
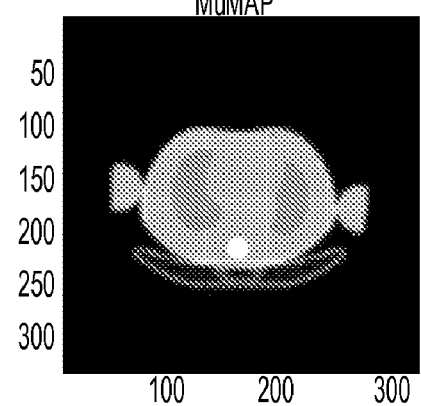

At step 170, the clean sinogram (with background removed) is corrected for attenuation using the attn.a factors (see μ-map, FIG. 2E), to obtain a fully corrected final sinogram (final.s). At step 180, an image (image.v) is reconstructed from the fully corrected final sinogram finales, using a known reconstruction algorithm such as Filtered Back Projection (FBP), as shown in FIG. 2D.

Figure 4:
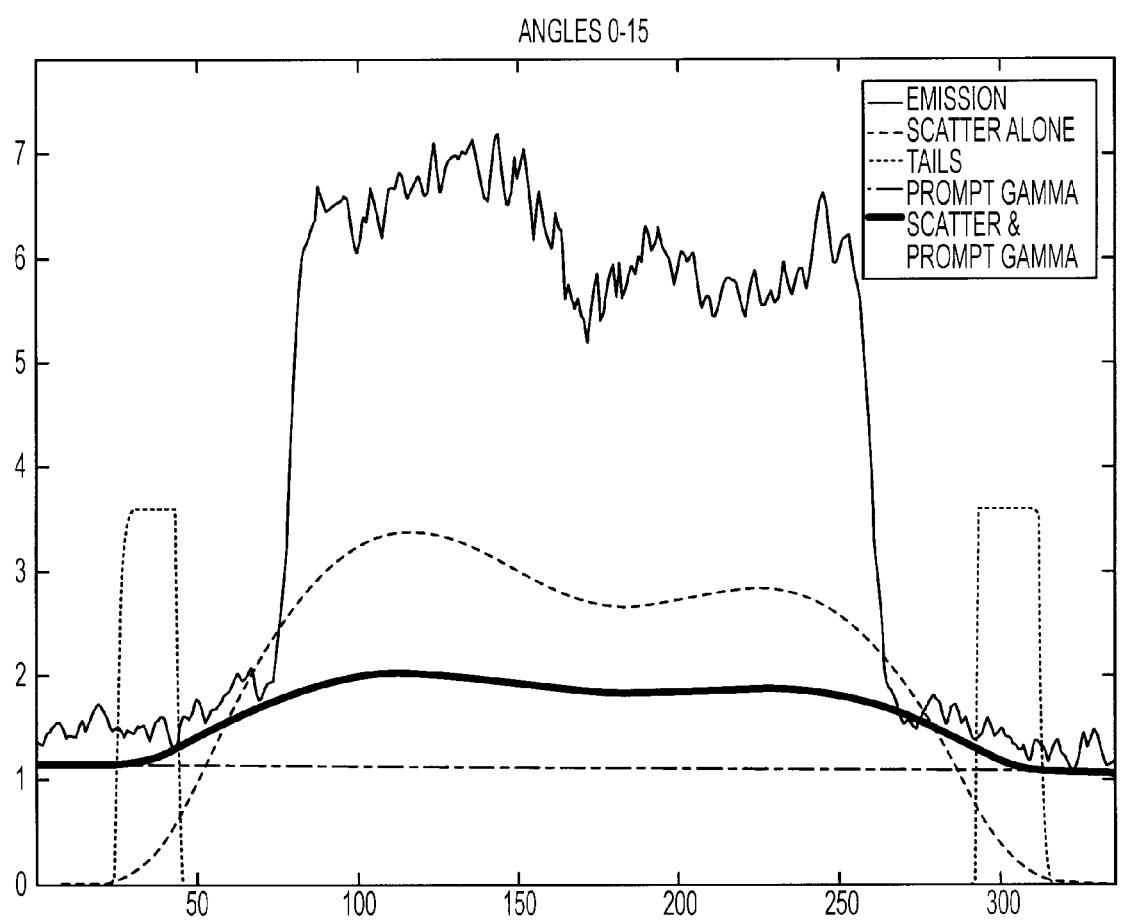
FIG. 4 is a graph of distributions of emission, least-squares-fit, and scatter tail data over a selected displacement angle range.

The performance of the least-squares fit of the randoms and scatter models with respect to the sinogram scatter tails is shown in FIG. 4 for a displacement angle range from 0 to 15 degrees, wherein other angle ranges over a 0 to 180 range will show similar characteristics. The dot-dash line illustrates the estimation of prompt gamma background contained in the emission data in accordance with the invention, and the thick line illustrates the estimation of background taking into account the prompt gamma background. Also shown as a dashed line is how the background would be estimated (i.e., due to scatter alone) without knowledge of the prompt gamma component. As shown, the correction of emission PET data using the present invention provides a significantly more accurate background estimation including prompt gamma background than the prior art.

The invention having been thus described, it will be apparent to those skilled in the art that the same may be varied in many ways without departing from the spirit and scope of the invention. Any and all such variations are intended to be included within the scope of the following claims.

What is claimed is:

1. A method for correcting PET emission data for prompt gamma emission background, comprising the steps of:
   obtaining PET emission data outputted from a PET scanner;
   estimating scatter data included in said outputted PET emission data;
   calculating emission tail distribution data of said outputted PET emission data;
   estimating prompt gamma background in said outputted PET emission data;
   fitting said estimated prompt gamma background and estimated scatter data in said tail distribution data to obtain estimated background data; and
   subtracting said estimated background data from said outputted PET emission data to obtain corrected PET emission data.

2. A method for correcting PET emission data as set forth in claim 1, further comprising the step of normalizing the outputted PET emission data prior to estimating scatter data.

3. A method for correcting PET emission data as set forth in claim 1, further comprising the step of converting said outputted PET emission data from said PET scanner into an emission sinogram.

4. A method for correcting PET emission data as set forth in claim 3, wherein the step of estimating scatter comprises performing a scatter simulation on said emission sinogram to obtain a scatter sinogram.

5. A method for correcting PET emission data as set forth in claim 4, further comprising using attenuation data in said step of estimating scatter.

6. A method for correcting PET emission data as set forth in claim 4, wherein said step of calculating emission tail distribution data comprises using said scatter sinogram and attenuation data.

7. A method for correcting PET emission data as set forth in claim 1, wherein the step of fitting comprises performing a least-squares fit (LSF).

8. A method for correcting PET emission data as set forth in claim 1, further comprising the step of correcting said corrected PET emission data for attenuation using attenuation data obtained from said PET scanner, to obtain final PET emission data.

9. A method for correcting PET emission data as set forth in claim 8, further comprising the step of reconstructing a PET image from said final PET emission data.

10. A method for correcting PET emission data as set forth in claim 9, wherein the step of reconstructing comprises performing a filtered back-projection on said final PET emission data.

11. A method for correcting PET emission data as set forth in claim 1, wherein the step of calculating emission tail distribution data comprises using said estimated scatter data to calculate said emission tail distribution data.

12. A method for correcting PET emission data as set forth in claim 1, wherein the step of calculating emission tail distribution data comprises using attenuation data to calculate said emission tail distribution data.

13. A method for correcting PET emission data as set forth in claim 1, wherein the step of estimating prompt gamma background comprises calculating randoms data from singles rate data included in said outputted PET emission data and using said calculated randoms data to model prompt gamma background.

14. A method for correcting PET emission data as set forth in claim 1, wherein the step of estimating prompt gamma background comprises performing a prompt gamma background simulation and using said simulation to model prompt gamma background.

15. A method for correcting PET emission data as set forth in claim 1, wherein the step of estimating prompt gamma background comprises using singles data to model prompt gamma background.

* * * * *